(12) United States Patent
Holte

(10) Patent No.: US 7,185,604 B2
(45) Date of Patent: Mar. 6, 2007

(54) ORTHOPEDIC PET CUSHION

(76) Inventor: Debra Leah Holte, 861 S. Steele St., Denver, CO (US) 80209

( * ) Notice: Subject to any disclaimer, the term of this patent is extended or adjusted under 35 U.S.C. 154(b) by 0 days.

(21) Appl. No.: 10/822,481

(22) Filed: Apr. 12, 2004

(65) Prior Publication Data

US 2005/0224000 A1  Oct. 13, 2005

(51) Int. Cl.
*A01K 29/00* (2006.01)
(52) U.S. Cl. .................................. 119/28.5
(58) Field of Classification Search .......... 119/28.5, 119/171, 172, 173, 169
See application file for complete search history.

(56) References Cited

U.S. PATENT DOCUMENTS

| | | | | |
|---|---|---|---|---|
| 3,125,663 | A | * | 3/1964 | Hoffman ............... 219/217 |
| 3,902,456 | A | | 9/1975 | David |
| 3,934,552 | A | * | 1/1976 | Kulka ............... 119/482 |
| 3,953,566 | A | | 4/1976 | Gore |
| 3,968,530 | A | | 7/1976 | Dyson |
| 4,194,041 | A | | 3/1980 | Gore |
| 4,344,999 | A | | 8/1982 | Gohlke |
| 4,454,191 | A | | 6/1984 | von Blucher et al. |
| 4,525,409 | A | | 6/1985 | Elesh |
| 4,614,000 | A | | 9/1986 | Mayer |
| 4,706,313 | A | | 11/1987 | Murphy |
| 4,761,524 | A | | 8/1988 | Rautenberg et al. |
| 4,777,681 | A | | 10/1988 | Luck et al. |
| 4,780,921 | A | | 11/1988 | Lahn |
| 4,801,493 | A | | 1/1989 | Ferziger et al. |
| 4,847,142 | A | | 7/1989 | Twilley et al. |
| 4,961,982 | A | * | 10/1990 | Taylor ............... 428/91 |
| 5,002,014 | A | | 3/1991 | Albin |
| 5,119,763 | A | | 6/1992 | Crabtree |
| 5,136,981 | A | | 8/1992 | Barreto, II |
| 5,144,911 | A | | 9/1992 | Moore |
| 5,226,384 | A | | 7/1993 | Jordan |
| 5,249,320 | A | | 10/1993 | Moretz |
| 5,265,558 | A | | 11/1993 | Schonrock |
| 5,515,811 | A | | 5/1996 | McAllister |
| 5,521,273 | A | | 5/1996 | Yilgor et al. |

(Continued)

FOREIGN PATENT DOCUMENTS

EP           622018 A1  *  11/1994

OTHER PUBLICATIONS

Barbara Pritchard, Introducing the Pressure Support Surfaces from Kaylned, British Journal of Nursing, 2001, vol. 10, No. 21 pp. 1427-1431, United Kingdom.

(Continued)

*Primary Examiner*—Son T. Nguyen
(74) *Attorney, Agent, or Firm*—Edwin H. Crabtree; Ramon L. Pizarro

(57) ABSTRACT

An orthopedic cushion for a support humans and animals, particularly domestic pets, includes a plurality of layers including a padding layer of slow recovery visco-elastic foam providing the orthopedic advantages of reducing pressure points and facilitating blood flow, a supporting padding layer of material which supports the slow recovery visco-elastic foam while providing additional loft and cushioning, a protective liner of a flexible waterproof yet breathable material protecting the padding from liquids of all nature, and a washable fabric cover. The pet bed of the present invention is orthopedic, washable, stain-resistant, hypoallergenic, and comfortable.

21 Claims, 4 Drawing Sheets

U.S. PATENT DOCUMENTS

| | | | |
|---|---|---|---|
| 5,539,072 | A | 7/1996 | Wu |
| 5,588,393 | A | 12/1996 | Heilborn, II |
| 5,660,918 | A | 8/1997 | Dutta |
| 5,685,257 | A | 11/1997 | Feibus |
| 5,715,722 | A | 2/1998 | Komrath |
| 5,724,911 | A | 3/1998 | McAllister |
| 5,836,654 | A * | 11/1998 | DeBellis et al. ....... 297/452.41 |
| 6,116,059 | A | 9/2000 | Rock et al. |
| 6,139,941 | A | 10/2000 | Janevies et al. |
| 6,173,675 | B1 | 1/2001 | Licciardo |
| 6,196,156 | B1 * | 3/2001 | Denesuk et al. ........... 119/28.5 |
| 6,391,935 | B1 | 5/2002 | Hager et al. |
| 6,495,612 | B1 | 12/2002 | Corzani et al. |
| 6,498,201 | B1 | 12/2002 | Corzani et al. |
| 6,508,200 | B1 | 1/2003 | Remis |
| 6,534,561 | B1 | 3/2003 | Corzane et al. |
| 6,645,887 | B2 | 11/2003 | Kocinee |
| 6,653,363 | B1 | 11/2003 | Tursi, Jr. et al. |

OTHER PUBLICATIONS

Liz White, Contributing Editor, Viscoelastic Foam Mattresses/ Marketing Hype or Molecular Miracle, Orethane Technology, Dec. 2001/Jan. 2002 vol. 18 No. 6 pp. 22-27. United States.

Atnin K. Habboub, PhD. Thermal Evaluation of Body Support Systems Using Thermogrammetry and Interfacial Temperature Sensing, 13[13] International Conference on Thermal Engineering an Thermogrammetry, Jun. 18-20, 2003. Budapest Fungry.

Julie Samms, High Moisture Vapor Transmission Thermoplastic Polyurethanes, Noveon, Inc, 9911 Brecrsville Road, Cleveland, Ohio 44141-3247 United States.

Larry Johnson and Dirk Schultz, Breathable TPE Films for Medical Applications, Medical Device and Diagnostic Industry Magazine Jul. 2000 United States.

Natalie Peterson, Mattresses as Vecters of Nosocomial Infection, Winona MSUS, United States.

Quoc Truong & Shantha Sarangapani, Devlepment of Elagstomeric Selectivity Permeable Membranes for Chemical/Biological Protective Clothing, Natik Soldier Center (NSC) Natik, MA, United States.

Proctor and Gambl, Low Viscosity Thermoplastic Compositions for Liquid-Impermeable, Vapor-Structures, Cincinnati Ohio, United States.

NC State University, 100% Cotton Moisture Management, Cotton Incorporated Journal of Textile and Appeal Technology Management, vol. 2, Issue 3 Summer 2002, Abstract, United States.

House of Dust Mite Allergen Avoidance—Editorial. British Medical Journal, Oct. 24, 1998, United Kingdom.

* cited by examiner

ORTHOPEDIC PET CUSHION

BACKGROUND OF THE INVENTION

1. Field of the Invention

The present invention relates in general to a pet cushion and more particularly, but not by way of limitation, to a pet cushion of orthopedic slow recovery visco-elastic foam providing orthopedic support, with a protective liner of a waterproof, breathable, flexible material enclosing the visco-elastic foam padding and the support padding while protecting the padding materials from liquids of all nature yet allowing for airflow and breathability of the padding layers it serves to enclose.

2. Description of the Prior Art

Pets are an important part of the family. Pet owners desire to provide the most comfortable pet cushions and beds as possible; particularly as our pets age this becomes even more important. Older animals often suffer from arthritis, and/or joint and muscle problems making sleeping or laying down for the animal uncomfortable. Most pet cushions are made with a padding material and a fabric cover, but do not address any orthopedic aspects for the pet.

Typically most pet cushions are made with common polyurethane foam. Common polyurethane foams (high resilience foams) are formulated to be resilient, resisting pressures and pushing against the source of impression. Logically, the foams recovery pressure is greatest at point were the subject is causing the greatest impression (e.g. hips, shoulders, leg joints). With seating, sleeping and other cushioning support surfaces, those pressures generated by common foam become sources of discomfort, as circulation is constricted by the upward force of the foam. These pressure points can, in clinical terms, contribute to the breakdown of skin resulting in the development of pressure ulcers.

Manufactured by an exclusive process, slow recovery visco-elastic foam is a unique and separate category of foam having characteristics different than all other types of foam. Slow recovery visco-elastic foam can double the surface contact area decreasing the pressure on bony prominences and facilitating blood flow. Slow recovery visco-elastic foam possesses the characteristics of high energy absorbent properties and temperature softening behavior. These properties produce a fluid and firm effect so that the material dissipates energy away from the body. These qualities provide for an exceptionally comfortable cushion as well as being orthopedically beneficial. As referenced in *Introducing the Pressure Support Surfaces from Kaymed* by Pritchard, Barbara in The British Journal of Nursing, 2001, Vol 10, No. 21.

Slow recovery visco-elastic foam is a polymer with a gel-like feel which, through its sensitivity to temperature, recognizes shape and pressure and adjusts to distribute load as evenly as possible. It simulates a floatation effect. This provides the orthopedic effect of reducing pressure points while giving additional comfort to the animal using the cushion.

Typically animal cushions in the prior art use a cushioning material of polyester, nylon, high resilience foam, or cotton and possibly a liner which encloses the padding materials. The cushioning materials, without a waterproof liner, can absorb liquids such as urine, blood, animal saliva, and other spilled liquids to the point of saturation making the cushion unsanitary and unhealthy. After a period of use, these beds become foul smelling. In time, the cushion will promote bacterial growth due to the moisture and the body heat of the animal as well as possibly infested with mites and fleas. Cushions can be difficult if not impossible to wash due to their size or material of construction. If the cushion cannot be cleaned, the only remedy is to replace the entire padding which can become costly. Typically, if the prior art had a liner component enclosing the padding materials it was at best of a water repellent nature only and thus not impermeable to fluids, or of an absorbent nature trapping and retaining the fluid.

Technology has introduced numerous high performance fabrics often used in performance outerwear or tents. Waterproof, breathable, and flexible fabrics are now manufactured by numerous sources, under numerous brand names, and are easily available to consumers. These fabrics achieve the waterproof qualities by a close weave fabric, or rely upon either the hydrophilic (water loving) or microporous qualities of materials which come as either a coating or a laminated film.

The quality of breathability is achieved as the molecular chains of hydrophilic material are used as stepping stones by water molecules. The molecules are passed from chain to chain by the force of the temperature/heat differential, until they are released to the outside. Water droplets cannot pass back across the fabric for it is non-porous. These microporous materials are created to have tiny holes within their structure. These holes are large enough for water vapor molecules to pass through yet many times too small to allow the passage of water droplets. A protective liner of a waterproof, breathable, flexible material would protect the cushion padding from absorbing liquids yet allow for airflow which maintains the loft of the padding materials while maintaining the comfort of the cushion long term. In addition, these fabrics are strong, durable, and resist odors and stains making them an ideal fabric of a protective liner in a pet cushion.

Most dirt contains oil. As polyester and nylon are both oil-based fibers, they are attracted to oily dirt, creating a bond between the dirt and the fiber, making it difficult to wash successfully. When dirt falls on hydrophilic fabrics, it rests on a bed of hydrophilic molecules keeping dirt away from the oil-based fabrics. The hydrophilic molecules attract and draw water and soap under the dirt allowing it to easily lift off. Prior art using polyester or nylon materials would prove more difficult to clean than the waterproof, breathable, flexible fabric suggested in the present invention.

There are no examples in prior art which combine slow recovery visco-elastic foam with a protective liner of a waterproof, breathable, flexible material in a cushion or a pet cushion.

A variety of pet cushions, beds or pads are available for domestic animals. U.S. Pat. No. 3,902,456 granted to David features a cloth-covered cushion.

U.S. Pat. No. 5,002,014 granted to Albin features woven polyester strands coated with polyvinyl chloride impervious to liquid and uses polystyrene beads as the cushioning material.

U.S. Pat. No. 5,119,763 granted to Crabtree features an orthopedic pet bed which the orthopedic support is from the quilting pattern fashioned on the filling material.

U.S. Pat. No. 5,144,911 granted to Moore features moisture repelling mattress liner and a water repellent cover with the four basic components which are detachable and removable from each other.

U.S. Pat. No. 5,226,384 granted to Jordan features animal beds whose main functions are pest-resistance and damage resistance using a KEVLAR aramid sheet and a MYLAR polyester sheet. Since neither KEVLAR nor MYLAR are soft comfortable fabrics, a removable cushion is place on top of the shell in order to offer comfort to the animal. Neither KEVLAR nor MYLAR is a flexible material, and MYLAR is very difficult to cut in order to construct the animal bed.

U.S. Pat. No. 5,265,558 granted to Schonrock features molding a one-piece foam bed with a liquid-impermeable closed pore skin. This bed can be used with or without a cover.

U.S. Pat. No. 5,515,811 granted to McAllister features a cushion for an animal, preferably a cat, which is a material of a matted web of layered, electrostatic fibers. This cushion is uncovered.

U.S. Pat. No. 5,588,393 granted to Heilborn II is a pet bed of a collapsible nature.

U.S. Pat. No. 5,685,257 granted to Fiebus features the use of several absorbent layers under the cushion cover with the center most layers being fluid impermeable.

U.S. Pat. No. 5,715,772 granted to Kamrath et al. features an absorbent pad for absorbing pet urine with a one-way moisture barrier.

U.S. Pat. No. 5,724,911 granted to McAlister features raw, unwoven, uncovered polyester.

U.S. Pat. No. 6,173,675 granted to Licciardo features aromatherapy to enhance certain behaviors of the animals that use the mat.

U.S. Pat. No. 6,508,200 granted to Remis features a support cushion wherein the variable support is from helical springs.

A variety of support pads and mattresses are available. U.S. Pat. No. 3,968,530 granted to Dyson features a gel-like fluid; U.S. Pat. No. 4,614,000 granted to Mayer features conical-shaped bubble supports; U.S. Pat. No. 4,706,313 granted to Murphy features foam blocks that can be selectively placed; U.S. Pat. No. 4,777,681 granted to Luck, et al. features foamed material with a plurality of slits; U.S. Pat. No. 4,780,921 granted to Lahn, et al features a cover for a therapeutic support cushion having two separate chambers; and U.S. Pat. No. 5,249,320 granted to Moretz features a reservoir for moisture.

Such pet cushions, mattresses, and mats have been introduced with varying degrees of success. The prior art pet beds however, fail to address orthopedic benefits or the protective benefits of a waterproof yet breathable liner in a pet cushion. The need has arisen for a pet cushion that offers the orthopedic benefits of slow recovery visco-elastic foam with a protective liner that allows the visco-elastic foam to breath while protecting it from liquids of all kinds. Visco-elastic foam is a state-of-the-art material providing the user the therapeutic benefits of even pressure distribution without constricting blood circulation and thereby lessening the risk of pressure points and user discomfort. These qualities provide for an exceptionally comfortable cushion as well as being therapeutically beneficial for animals suffering from arthritis and/or joint and muscle ailments. The liner material takes advantage of the current high performance materials offering waterproof yet breathable and easily cleanable characteristics which creates a hygienic environment for the cushion user.

SUMMARY OF THE INVENTION

The primary object of the present invention is to provide a orthopedic pet cushion, made with slow recovery visco-elastic foam, that will overcome the shortcoming of the prior art devices.

Another object of the present invention is to use a material known to have the orthopedic properties of sensitivity to temperature, recognition of shape and pressure, and the ability to adjust and distribute load as evenly as possible which provides the orthopedic benefits of decreasing the pressure on the bony prominences and facilitating blood flow. Currently the only material known to have the above listed qualities is slow recovery visco-elastic foam.

Another objective of the present invention to provide an additional second padding layer to the slow recovery visco-elastic foam padding which will give the very flexible visco-elastic foam padding additional support and stability while adding additional overall cushioning for added comfort.

It is another object of the present invention to provide protection of the padding materials from liquids by a waterproof liner. This waterproof material used for the liner may naturally offer oleophobic, anti-dust mite, anti-odor, anti-bacterial, anti-stain, or anti-static properties in addition to its waterproof property.

It is yet another object of the present invention to provide a waterproof liner material that is also breathable and flexible. The ability of the waterproof liner to breathe allows for airflow and maintains cushion loft for continuing comfort. The flexibility of the liner material is necessary so the liner does not hamper the comfort or cushioning ability of the padding it serves to enclose and protect.

It is another object of the present invention to provide protection of the padding materials. This protection is achieved by a protective liner of a waterproof, breathable, flexible material which totally encloses all padding materials and is sealed shut by an appropriate means such as sewing, gluing, thermal bonding or the like. This protective liner is sealed around the padding materials in such a tight and close-fitting manner, that it prevents the two padding materials from shifting or moving about within the protective liner.

It is yet another object of the present invention to provide an outer cover of a material that is soft, comfortable, hypoallergenic, absorbent, resistant to the adherence of stains, and is highly resistant to breakage or tearing in any direction. The resealable closure allows for easy removal of the cover for washing. The cover is made of a fabric that may be conventionally laundered repeatedly.

To that end, an orthopedic cushion, for pets or humans, which includes a cushion formed from a plurality of layers including two padding layers, one of slow recovery visco-elastic foam and the second of a material that supports the visco-elastic foam while adding additional padding. Then a protective liner made from a waterproof, breathable, flexible material which completely encloses the two padding layers and is sealed around the padding layers in such a tight and close-fitting manner as to prevent shifting or moving about of the padding layers within the protective liner. Finally, around the enclosed padding layers and their protective liner, is a soft comfortable washable cover. This outer cover may be easily removed for washing.

The second supporting padding layer may be made from a textile-based, foam, or rubber material.

The waterproof, breathable, flexible protective liner material may achieve the properties of waterproof and breathablilty by a number of methods such as, but not limited to, utilizing a hydrophilic coating or laminate, a microporous coating or laminate, a bi-component coating or laminate, a monolithic membrane, a moisture-vapor-transmission (MVT) membrane, or a microfiber of sufficiently close weave as to be waterproof and breathable.

The outer washable cover is comprised of a top surface, a bottom surface and peripheral side walls between the top and bottom surfaces. This outer fabric cover has a releasable closure so that fabric cover may be easily removed washing.

The orthopedic cushion may be constructed in any geometric shape deemed necessary by the user's space needs. Suggested shapes would include, but not limited to, square, round, rectangular, triangular, semi-circle, or pie-shaped.

Further objects of the invention will appear as the description proceeds.

To accomplish the above and related objects, this invention may be embodied in the form illustrated in the accompanying drawings, attention being called to the fact, however, that the drawings are illustrative only, and that changes may be made in the specific construction illustrated and described within the scope of the appended claims.

DETAILED DESCRIPTION OF THE PREFERRED EMBODIMENT

Figure 1:
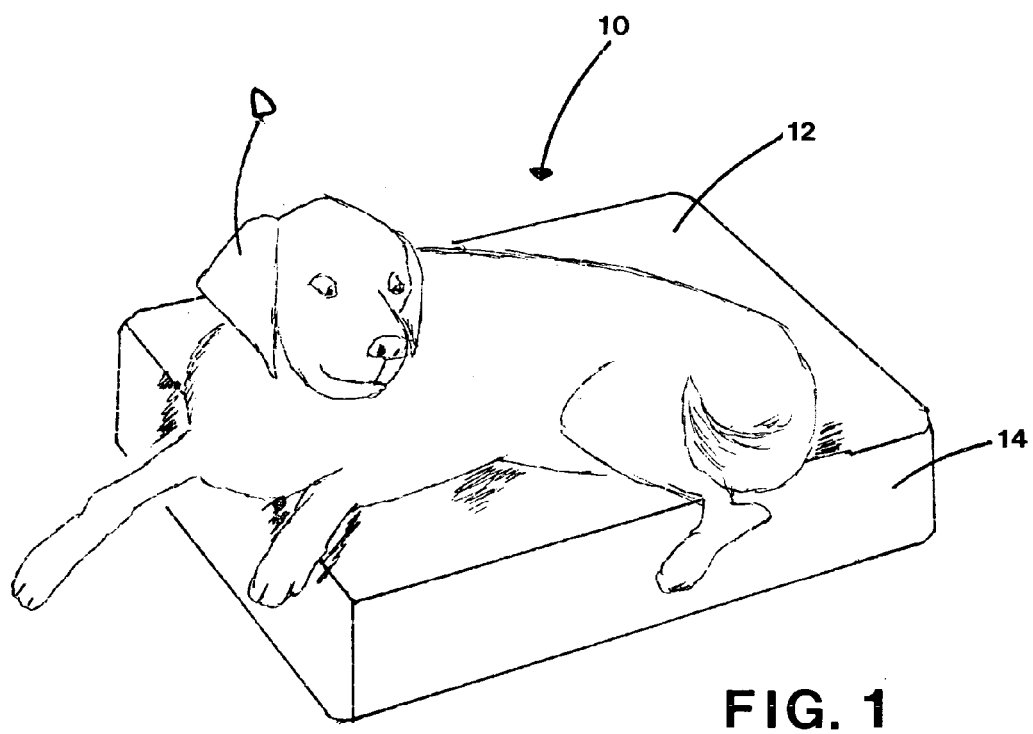
FIG. 1 is a perspective view of an orthopedic support cushion for humans and animals, particularly domestic pets, according to the preferred embodiment of the present invention.

Turning now to the drawings and, more particularly, to FIG. 1, an orthopedic support cushion for humans and animals, and, more particularly, domestic pets, is illustrated generally in its simplest embodiment comprises a cushion 10, may be formed as a generally rectangular body having a top outer cover layer 12 and a fabric side panel 14.

Figure 2:
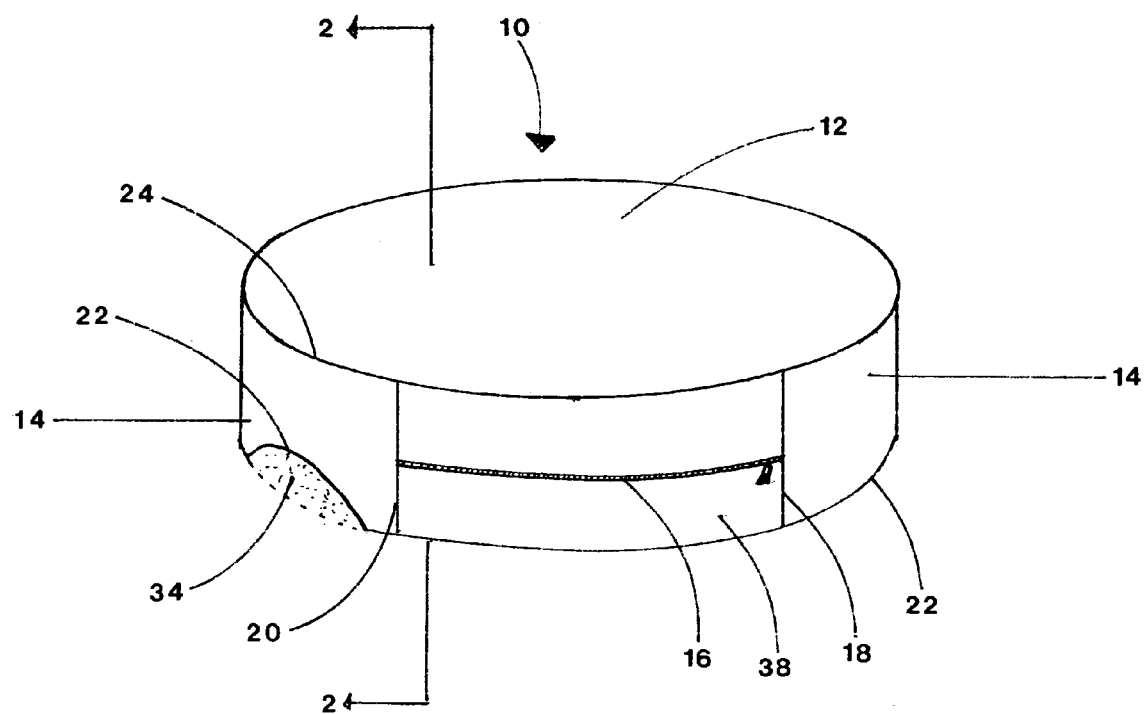
FIG. 2 is another perspective view of an orthopedic support cushion for humans and animals, particularly domestic pets, according to the preferred embodiment of the present invention.

FIG. 2 the orthopedic support cushion for humans and animals, and, more particularly, domestic pets, is illustrated generally at 10 and may be formed as a generally round body having a outer top cover layer 12 attached to side panels 14 and 38 by a stitched seam 24 and attached to the second covering bottom layer 34 by stitched seam 22. The completed side panel is composed of two panels: first side panel 38 is a panel containing a resealable closure, a the second side panel 14; whereby side panel 38 is attached to side panel 14 by stitched seams 18 and 20 and can be disposed to extend around the perimeter or circumference of the top and bottom panels. It is preferred the cover fabric used for the cover of the cushion of the present invention is soft, comfortable, and hypoallergenic, yet absorbent and also resistant to the adherence of stains and is highly resistant to breakage or tearing in any direction. It is further preferred the resealable closure mechanism 16 be of sufficient length to allow for easy removal of the cover for washing. Lastly it is preferred the cover be made of a fabric that can be conventionally laundered.

Figure 3:
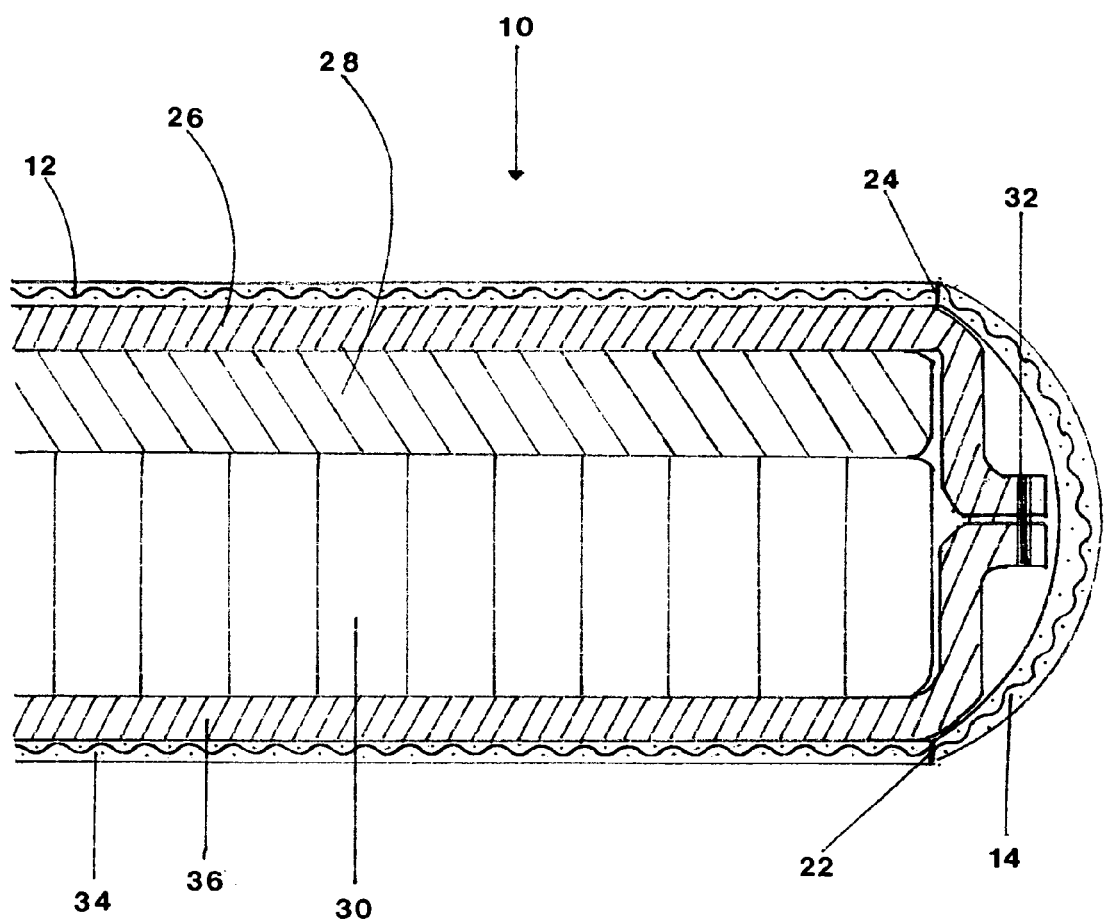
FIG. 3 is a cross-sectional view of an orthopedic support cushion illustrated in FIG. 2 taken along lines 2—2 thereof.
Figure 4:
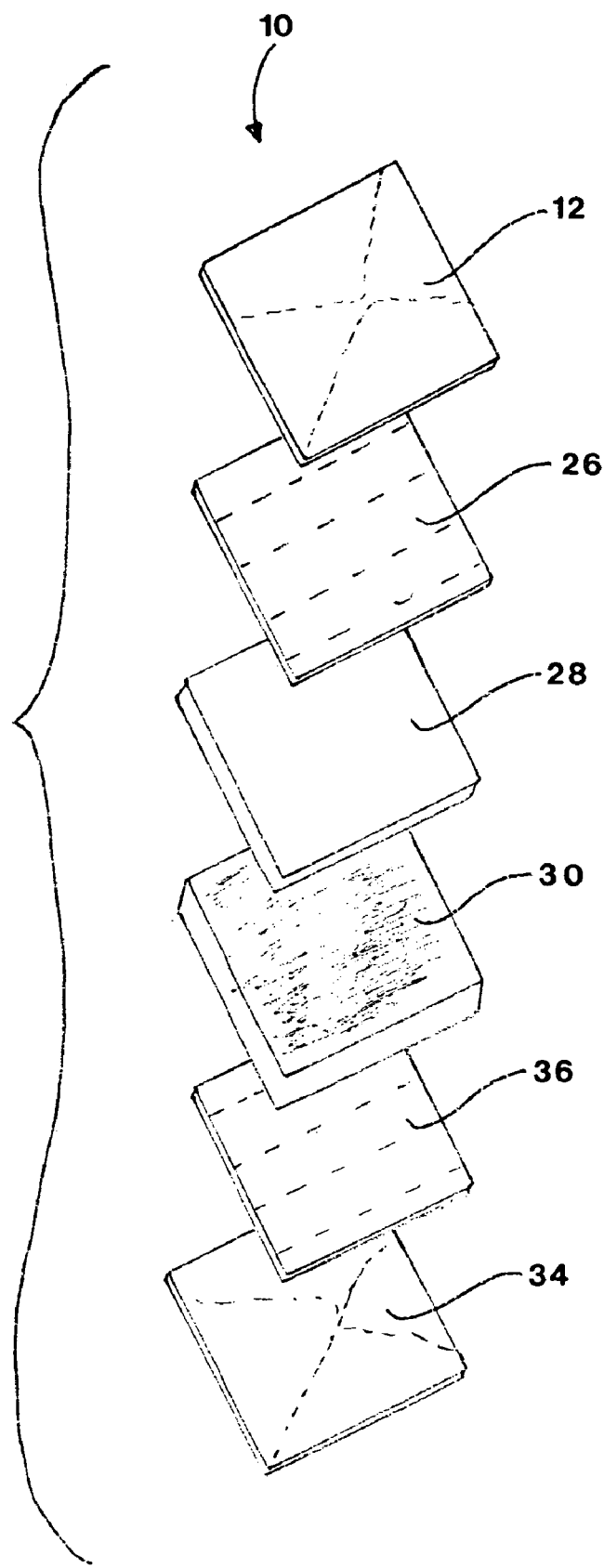
FIG. 4 is an exploded view of an orthopedic support cushion illustrated in FIG. 1 and FIG. 2.

As seen in FIGS. 3 and 4 of the preferred embodiment of the orthopedic support cushion of the present invention is formed from a plurality of layers which are retained in a closely adjacent relationship with each layer being formed of sheet material. Each layer can be generally rectangular, square, round, triangular, or pie shaped and extends the full width and breadth of the cushion body 10. The present invention includes an outer cover layer 12 which is disposed closely adjacent a first intermediate layer 26. The first intermediate layer 26 is formed from a waterproof, breathable, flexible material. Following in succession inwardly toward the center of the cushion 10, a second intermediate layer 28 is disposed closely adjacent the first intermediate layer 26. The second intermediate layer 28 is formed from slow recovery visco-elastic foam.

An inner layer 30 is disposed closely adjacent the second intermediate layer 28. The inner layer 30 is formed from padding material providing support, loft and cushioning to the cushion. A fourth intermediate layer 36 is disposed closely adjacent the inner layer 30 and is formed from a waterproof, breathable, flexible material similar to the material from which the first intermediate layer 26 is formed. Finally a second covering bottom layer 34 is disposed closely adjacent the fourth intermediate layer 36 and is formed from the material which comprises the first cover 12.

As previously mentioned a side panel composed of 14 and 38 is seamed to the first covering layer 12 by a stitched seam 24 as well as seamed to the second covering bottom layer 34 by stitched seam 22 and extends around the entire perimeter of cushion 10. The first intermediate layer 26 is sealed closed by sewing, gluing, thermal bonding or the like by seam 32, to fourth intermediate layer 36 forming a complete bond which encloses second intermediate layer 28 and inner layer 30 forming a waterproof barrier and retarding relative movement between said layer 28 and said layer 30.

It should be understood by those skilled in the art that the cushion 10 of the present invention may be formed with the first intermediate layer 26 and fourth intermediate layer 36 may be a single sheet folded in half without departing from the sprit and scope of the invention.

In operation, the cushion of the present invention can be placed on the floor and may support a dog D as seen in FIG. 1 or other domestic pet. Further the cushion 10 may be used for children or adults.

The present cushion provides many advantages. Slow recovery visco-elastic foam offers the user of the cushion the advantages of sensitivity to temperature, recognition of shape and pressure, and the ability to adjust and distribute load as evenly as possible which provides the orthopedic benefits of decreasing the pressure on the bony prominences and facilitating blood flow. The cushion fabric cover is of an absorbent fabric that may be conventionally laundered repeatedly while retaining its soft, comfortable, hypoallergenic qualities. The inner liner of a waterproof, breathable, flexible material will not absorb liquids from the absorbent cover; thereby protecting the enclosed padding material which serves to extend the life of the orthopedic pet cushion. Most stains on the liner can be spot cleaned. Since this liner is waterproof, yet able to breathe, it often will naturally provide a measure of odor, pest, static and bacterial resistance. The ability of the liner to breathe maintains the loft and comfort of the padding materials. Finally, most slow recovery visco-elastic foam manufactured today in the United States is fire retardant. By the above, the present invention provides a unique and beneficial orthopedic pet cushion.

It will therefore be readily understood by those persons skilled in the art that the present invention is susceptible of a broad utility and application. Many embodiments and adaptations to the present invention other than those herein described, as well as many variations, modifications and equivalent arrangements, will be apparent from or reasonably suggest by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or other wise to exclude any such other embodiments, adaptations, variations, modifications and equivalent arrangements, the present invention be limited only by the claims appended hereto and the equivalents thereof.

I claim:

1. A cushion for a domestic pet, the cushion comprising:
   a slow recovery, porous, visco-elastic foam padding layer;
   a supporting layer, said supporting layer made of a stabilizing material for supporting said visco-elastic foam padding layer thereon, a top of said supporting layer received next to a bottom of said visco-elastic foam padding layer;
   a waterproof, breathable, flexible material protective liner, said protective liner received over a top of said visco-elastic foam padding layer and over a bottom of said supporting layer, said protective liner preventing an absorption of liquids from the domestic pet into the top of said visco-elastic foam padding layer and into the bottom of said supporting layer, said protective liner allowing airflow to pass through the cushion for maintaining loft of said visco-elastic foam padding layer and said supporting layer; and
   a washable fabric cover, said washable fabric cover enclosing said visco-elastic foam padding layer, said supporting layer, and said protective liner.

2. The cushion as recited in claim 1, wherein the supporting padding layer is comprised of a textile-based material.

3. The cushion as recited in claim 1, wherein the supporting padding layer is comprised of a foam material.

4. The cushion as recited in claim 1, wherein the supporting padding layer is comprised of a rubber material.

5. The cushion as recited in claim 1, wherein said waterproof, breathable, and flexible protective liner is comprised of a hydrophilic laminate.

6. The cushion as recited in claim 1, wherein said waterproof, breathable, and flexible protective liner is comprise of a hydrophilic coating.

7. The cushion as recited in claim 1, wherein said waterproof, breathable, and flexible protective liner is comprised of a microporous laminate.

8. The cushion as recited in claim 1, wherein said waterproof, breathable, and flexible protective liner is comprised of a microporous coating.

9. The cushion as recited in claim 1, wherein said waterproof, breathable, and flexible protective liner is comprised of a bi-component laminate.

10. The cushion as recited in claim 1, wherein said waterproof, breathable, and flexible protective liner is comprised of a bi-component coating.

11. The cushion as recited in claim 1, wherein said waterproof, breathable, and flexible protective liner comprises a material fabricated from a microfiber of a sufficiently close weave to be waterproof and breathable.

12. The cushion as recited in claim 1, wherein said waterproof, breathable, and flexible protective liner is comprised of a material fabricated with a monolithic membrane.

13. The cushion as recited in claim 1, wherein said waterproof, breathable, and flexible protective liner is naturally oleophobic, anti-dust mite, anti-odor, anti-bacterial, anti-stain, and anti-static.

14. The cushion as recited in claim 1, wherein said fabric cover has a releasable closure so that said fabric cover may be removed from the said padding of slow recovery visco-elastic foam, said padding of stabilizing support material, and said protective liner, for washing.

15. The cushion as recited in claim 1, wherein said fabric cover is comprised of a top surface, a bottom surface, and peripheral side walls disposed between said top and bottom surfaces.

16. The cushion as recited in claim 1, wherein said waterproof, breathable, and flexible protective liner is sealed closed around said padding layer of slow-recovery visco-elastic foam and said supporting padding layer in such a close-fitting and tight manner that the protective liner does not allow for the inner padding layers, of said slow recovery visco-elastic foam and said supporting stabilizing material, to shift or move about within the said protective liner.

17. A cushion for a domestic pet, the cushion comprising:
    a slow recovery, porous, visco-elastic foam padding layer;
    a supporting layer, said supporting layer made of a stabilizing material for supporting said visco-elastic foam padding layer thereon, a top of said supporting layer received next to a bottom of said visco-elastic foam padding layer;
    a waterproof, breathable, flexible moisture-vapor-transmission (MVT) material protective liner comprising upper and lower layers that are fastened together at their peripheral edges, said protective liner received over a top of said visco-elastic foam padding layer and over a bottom of said supporting layer, said protective liner preventing an absorption of liquids from the domestic pet into the top of said visco elastic foam padding layer and into the bottom of said supporting layer, said protective liner allowing airflow to pass through the cushion for maintaining loft of said visco-elastic foam padding layer and said supporting layer; and
    a washable fabric cover, said washable fabric cover enclosing said visco-elastic foam padding layer, said supporting layer, and said protective liner.

18. The orthopedic pet cushion as recited in claim 17, wherein said protective liner of breathable, waterproof, MVT material is comprised of a close-weave fabric of a sufficiently close weave to be waterproof and breathable.

19. The orthopedic pet cushion as recited in claim 17, wherein said breathable, waterproof, flexible, and MVT membrane material of said protective liner is naturally oleophobic, anti-dust mite, anti-odor, anti-bacterial, anti-stain, and anti-static.

20. The orthopedic pet cushion as recited in claim 17, wherein said outer fabric cover is comprised of a top surface, a bottom surface, and peripheral side walls disposed between said top and bottom surfaces.

21. The orthopedic pet cushion as recited in claim 17, wherein said protective liner of flexible, breathable, waterproof, MVT membrane material is sealed closed around said padding layer of slow-recovery visco-elastic foam and said supporting padding layer, in such a close-fitting and tight manner that the protective liner does not allow for the padding layers, of said slow recovery visco-elastic foam and said supporting padding, to shift or move about within the said protective liner.

* * * * *